United States Patent [19]

Williams

[11] Plant 4,580

[45] Jul. 29, 1980

[54] MINIATURE ROSE PLANT

[76] Inventor: Ernest D. Williams, 1510 Lebanon Ave., Dallas, Tex. 75208

[21] Appl. No.: 30,996

[22] Filed: Apr. 18, 1979

[51] Int. Cl.[2] ..... A01H 5/00

[52] U.S. Cl. ..... Plt./7

[58] Field of Search ..... Plt./7

*Primary Examiner*—Robert E. Bagwill
*Assistant Examiner*—James R. Feyrer

[57] ABSTRACT

The subject of the present disclosure is a new and distinct variety of miniature rose plant characterized by the bright yellow buds and flowers which become overlaid or blended with red as they mature and by the profusion of bloom.

1 Drawing Figure

1

The present invention relates to a new and distinct variety of hardy, dwarf bush type rose plant of the miniature class; the variety being primarily characterized—as to novelty—by yellow buds and flowers which become overlaid or blended with red as they mature, the general color effect being similar to Circus, A Floribunda variety (U.S. Plant Pat. No. 1,382, expired).

The variety is further characterized by:

An abundance of bloom, with flowers usually borne singly—sometimes several to the stem.

Slight fragrance.

A plant which is vigorous, of rounded somewhat upright shape with semi-glossy, small foliage with pointed leaflets; the buds and flowers being similar in form to Over the Rainbow (miniature—U.S. Plant Pat. No. 3,472), but averaging slightly larger in size.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Starburst (U.S. Plant Pat. No. 2,974) as the seed parent and Over the Rainbow (miniature—U.S. Plant Pat. No. 3,472) as the pollen parent.

Subsequent to origination of the variety I successfully reproduced it, at my nursery located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Carnival parade.

2

Flowers borne: Usually singly, sometimes several together on slender wirey stems.

Quantity of bloom: Abundant both outside and in greenhouse.

Bud:

*Peduncle.*—Medium length; slender but sturdy; erect; medium green, sometimes tinted bronze (outdoors); Hairs — some.

*Before calyx breaks.*—Size — small. Form long; pointed with several foliaceous apendages and some tiny hairs on surface of bud; with foliaceous parts extending beyond the tip of the bud equal to one-half or less of its length. Color — medium green, occasionally tinted with bronze (outdoors).

*As calyx breaks.*—Color — deep yellow — near Saffron Yellow 7/2 or lighter and often tinted greenish yellow at base, with a splash or two of red on area of bud first exposed to sunlight. Opening: opens well in all weather.

Bloom:

*Size when fully open.*—Small, averaging about $1\frac{1}{4}$–$1\frac{1}{2}$".

*Petalage.*—Double — averaging about 45 petals, arranged regularly plus sometimes several small petaloids.

Form.—High centered at first (Hybrid Tea form), becoming more open in the center, with petals reflexing loosely outward and downward. Open flowers show stamens.

Petals: Fairly thick; satiny on inside and on outside surface.

*Shape.*—Outside petals, broad lanceolate (nearly round) with rounded tip; intermediate — broad lanceolate with rounded tip; inside — lanceolate with rounded tip.

Color: Newly opened flower from a plant grown outdoors (Fall 1978), Dallas, Tex.

*Outside petals.*—Outside surface — near Saffron Yellow 7/2 or Buttercup Yellow 5/2 with small greenish yellow area at base. Inside surface — yellow — similar to outside surface but overlaid with more or less red and finishing near Currant Red 821/3 or similar color.

*Intermediate petal.*—Outside surface — similar to outside petal. Inside surface — similar to outside petal.

*Inner petal.*—Outside surface — similar to intermediate petal; inside surface — similar to intermediate petal. General color effect; newly opened flowers — rich yellow with petal tips overlaid with red or orange red. Three days open — color — more red area and deeper red color; petal reverse stays yellow but less brilliant. Behavior — opens well in all weather. Color — both the yellow and red are most intense under full sun. In plastic greenhouse flower remains yellow, with little or no red. Spent petals drop off. Flower longevity (Fall 1978) — plant in pot 6–8 days or longer. Cut flowers at living room temperature 4–5 days or longer.

Reproductive organs:

*Stamens.*—Fairly abundant, arranged regularly about pistils.

*Filaments.*—Varying length, medium long, yellow.

*Anthers.*—Well formed; yellow.

*Pollen.*—Moderate amount.

*Pistils.*—Average number.

*Styles.*—Fairly even; medium to short length; bunched; color — greenish.

*Ovaries.*—All enclosed in calyx.

*Hips.*—Few or none.

*Sepals.*—Permanent; spear shaped; recurved.

*Seed.*—Few or none.

Foliage:

*Leaves.*—Compound of five (sometimes three or seven) leaflets; fairly small; leathery; semi-glossy.

*Leaflets.*—Shape; broad, nearly oval; apex acute; base rounded or rounded acute. Margin serrate. Color: medium to dark green; new growth — normal (medium) green, often tinted bronze. Rachis: medium strength; upper side may have a few tiny short hairs, grooved; underside sparsely thorny with few or no tiny prickles. Stipules: fairly long; narrow to medium width; medium length; narrow points which turn out usually at about 45 degrees.

Growth:

*Habit.*—Dwarf; bushy; rounded; much branched.

*Growth.*—Free; vigorous; internodes short.

*Canes.*—Medium; slender; sturdy.

*Main stems.*—Color: medium green.

*Thorns.*—Average; slender; hooked slightly downward; color; brown. Prickles — few or none. Hairs — none.

*Branches.*—Color: medium green. Thorns: moderate number; medium length; slender; nearly straight, inclined slightly downward. Prickles: none. Hairs: none.

The miniature rose plant and its flowers as herein described may vary in slight detail due to climatic, soil and cultural conditions under which the variety may be grown; the present description being of the variety as grown at Dallas, Tex., and at Visalia, Calif.

The following is claimed:

1. A new and distinct variety of miniature rose plant of hardy, dwarf, bushy, rounded, much branched habit, substantially as illustrated, and described, characterized by buds and flowers of a rich yellow color, being of a shade generally near Saffron Yellow 7/2 or Buttercup Yellow 5/2 or lighter, the yellow color remaining on lower petal surface but the upper surfaces tending to become overlaid (beginning at petal tips) with orange red and becoming deep red at maturity, the bud and flower resembling the variety Over The Rainbow (U.S. Plant Pat. No. 3,472) in general form and size and the Floribunda variety Circus (U.S. Plant Pat. No. 1,382, expired) in coloring; and further characterized by a plant of vigorous and compact growth habit, easy to propagate from cuttings, with an abundance of small to medium size — semi-glossy foliage and an abundance of flowers usually borne singly but sometimes several together.

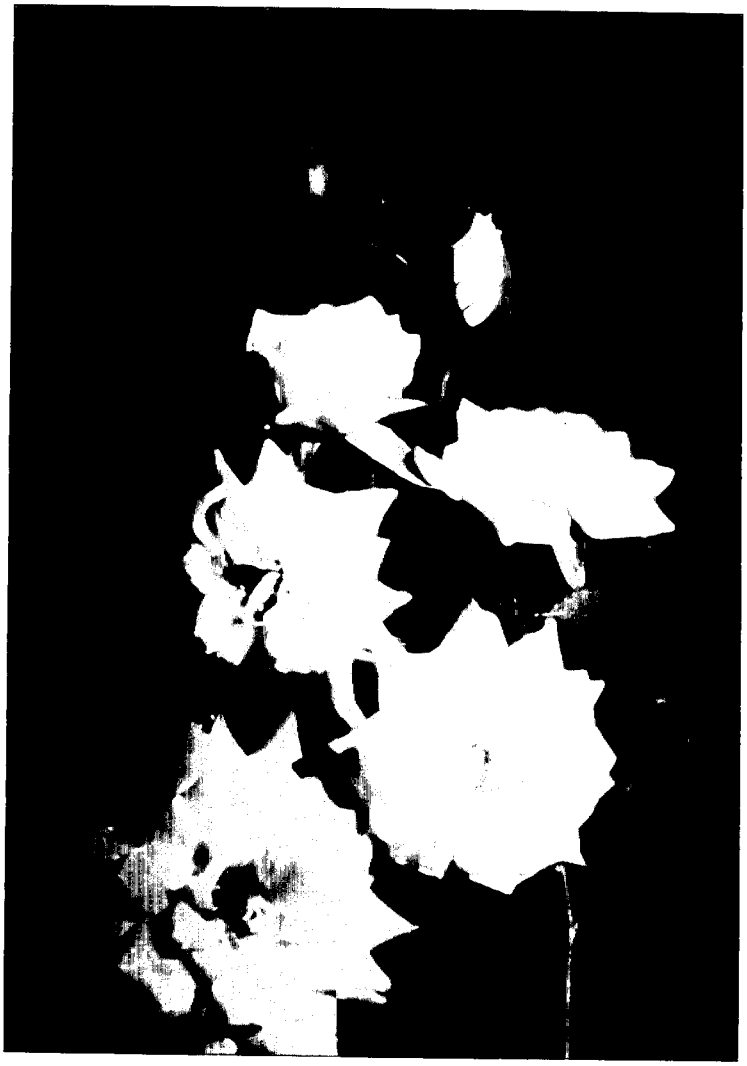

* * * * *